US006794357B1

(12) United States Patent
Bäckström et al.

(10) Patent No.: US 6,794,357 B1
(45) **Date of Patent: *Sep. 21, 2004**

(54) COMPOSITIONS FOR INHALATION

(75) Inventors: Kjell Göran Erik Bäckström, Lund (SE); Carl Magnus Olof Dahlbäck, Lund (SE); Peter Edman, Bjärred (SE); Ann Charlotte Birgit Johansson, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 08/736,267

(22) Filed: Oct. 24, 1996

Related U.S. Application Data

(63) Continuation of application No. 08/265,237, filed on Jun. 23, 1994, now abandoned.

(30) Foreign Application Priority Data

Jun. 24, 1993 (SE) ............................................ 9302198
Feb. 4, 1994 (SE) ............................................ 9400371

(51) Int. Cl.[7] .......................... A61K 38/00; A61K 9/14

(52) U.S. Cl. ............................... 514/2; 514/3; 514/12; 514/13; 424/489

(58) Field of Search .......................... 514/2, 3, 12, 13, 514/8, 11; 424/489, 852

(56) References Cited

U.S. PATENT DOCUMENTS

| | | | | |
|---|---|---|---|---|
| 2,992,645 A | | 7/1961 | Fowler | 128/208 |
| 3,014,844 A | | 12/1961 | Thiel | |
| 3,671,625 A | | 6/1972 | Altounyan | 424/45 |
| 3,911,138 A | * | 10/1975 | Clark | 424/352 |
| 4,232,002 A | | 11/1980 | Nogrady | 424/45 |
| 4,462,983 A | | 7/1984 | Azria et al. | 424/45 |
| 4,524,769 A | | 6/1985 | Wetterlin | |
| 4,534,345 A | | 8/1985 | Wetterlin | |
| 4,537,772 A | | 8/1985 | Alexander | 514/9 |
| 4,548,922 A | | 10/1985 | Carey et al. | |
| 4,613,500 A | | 9/1986 | Suzuki et al. | |
| 4,668,218 A | | 5/1987 | Virtanen | |
| 4,690,952 A | | 9/1987 | Kagatani et al. | |
| 4,731,360 A | | 3/1988 | Alexander | 514/201 |
| 4,746,508 A | | 5/1988 | Carey et al. | |
| 4,788,221 A | | 11/1988 | Kagatani et al. | |
| 4,847,298 A | | 7/1989 | Alexander | |
| 4,895,719 A | | 1/1990 | Radhakrishnan | |
| 4,900,730 A | | 2/1990 | Miyauchi | |
| 4,907,583 A | | 3/1990 | Wetterlin et al. | |
| 4,914,084 A | * | 4/1990 | Ecanow | 514/6 |
| 4,920,061 A | * | 4/1990 | Poynton | 436/526 |
| 4,926,852 A | | 5/1990 | Zoltan et al. | 128/200.23 |
| 4,959,358 A | | 9/1990 | Carey et al. | |
| 4,994,439 A | | 2/1991 | Longenecker | |
| 5,006,343 A | | 4/1991 | Benson et al. | |
| 5,011,678 A | | 4/1991 | Wang | |
| 5,118,494 A | | 6/1992 | Schultz | |
| 5,122,127 A | | 6/1992 | Stanley | |
| 5,122,376 A | | 6/1992 | Aliverti et al. | |
| 5,179,079 A | | 1/1993 | Hansen | |
| 5,192,548 A | | 3/1993 | Velasquez et al. | |
| 5,200,393 A | | 4/1993 | Weiner | |
| 5,202,129 A | | 4/1993 | Samejima et al. | |
| 5,254,330 A | | 10/1993 | Ganderton et al. | |
| 5,260,306 A | | 11/1993 | Boardman et al. | |
| 5,284,656 A | * | 2/1994 | Platz et al. | 424/435 |
| 5,288,498 A | | 2/1994 | Stanley et al. | |
| 5,320,094 A | | 6/1994 | Laube et al. | 128/203.12 |
| 5,341,800 A | | 8/1994 | Clark et al. | |
| 5,348,730 A | | 9/1994 | Greenleaf | |
| 5,349,947 A | | 9/1994 | Newhouse et al. | 128/203.21 |
| 5,352,461 A | | 10/1994 | Feldstein et al. | 424/493 |
| 5,354,562 A | | 10/1994 | Platz et al. | |
| 5,364,838 A | | 11/1994 | Rubsamen | |
| 5,376,359 A | | 12/1994 | Johnson | 424/46 |
| 5,376,386 A | | 12/1994 | Ganderton et al. | |
| 5,384,133 A | | 1/1995 | Boyes et al. | |
| 5,419,315 A | | 5/1995 | Rubsamen | |
| 5,437,271 A | | 8/1995 | Hodson et al. | |
| 5,451,569 A | | 9/1995 | Wong et al. | 514/3 |

(List continued on next page.)

FOREIGN PATENT DOCUMENTS

| | | |
|---|---|---|
| AU | 43556/93 | 1/1994 |
| CA | 2115065 | 6/1993 |
| DE | DK DD 261 096 A1 | 10/1988 |
| DE | DD 261 296 A1 | 10/1988 |
| EP | 0 023 359 | 7/1980 |
| EP | 0 023 359 A2 | 4/1981 |
| EP | 0 055 041 | 12/1981 |
| EP | 0 122 036 | 10/1984 |
| EP | 0 128 831 | 12/1984 |
| EP | 0 133 252 A2 | 2/1985 |
| EP | 0 200 383 | 4/1986 |
| EP | 0 225 189 | 11/1986 |
| EP | 0 312 052 A1 | 10/1987 |
| EP | 0 364 235 A1 | 4/1988 |
| EP | 0 272 097 | 6/1988 |
| EP | 0 360 340 | 3/1990 |
| EP | 0 455 463 | 6/1991 |
| EP | 0 383 751 | 9/1994 |
| GB | 837 465 | 6/1960 |
| GB | 1242211 | 8/1971 |

(List continued on next page.)

OTHER PUBLICATIONS

Kalinkova G N (International Journal of Pharmaceutics 187 (1) 1–15, 1999).*

(List continued on next page.)

*Primary Examiner*—Christopher S. F. Low
*Assistant Examiner*—David Lukton
(74) *Attorney, Agent, or Firm*—Fish & Richardson P.C.

(57) ABSTRACT

Disclosed herein are dry powder compositions comprising a pharmacologically active polypeptide and a surfactant, wherein at least 50% of the total mass of the polypeptide and the surfactant consists of primary particles having a diameter less than 10 microns. The compositions are suitable for inhalation from a dry powder inhaler device.

70 Claims, 2 Drawing Sheets

U.S. PATENT DOCUMENTS

| | | | |
|---|---|---|---|
| 5,458,135 A | 10/1995 | Patton et al. | 128/200.14 |
| 5,474,759 A | 12/1995 | Fassberg et al. | 424/45 |
| 5,482,032 A | 1/1996 | Smith et al. | |
| 5,482,706 A | 1/1996 | Igari et al. | |
| 5,506,203 A | 4/1996 | Bäckström et al. | 514/4 |
| 5,514,670 A | 5/1996 | Friedman | |
| 5,518,998 A | 5/1996 | Bäckström et al. | 514/3 |
| 5,607,915 A | 3/1997 | Patton | 514/12 |
| 5,658,878 A | 8/1997 | Bäckström et al. | 514/3 |
| 5,661,130 A | 8/1997 | Meezan et al. | 514/25 |
| 5,707,644 A * | 1/1998 | Illum | |
| 5,730,969 A | 3/1998 | Hora et al. | 424/85.1 |
| 5,747,445 A | 5/1998 | Bäckström et al. | 514/4 |
| 5,814,607 A | 9/1998 | Patton | 514/12 |
| 5,830,853 A | 11/1998 | Bäckström et al. | 514/4 |
| 5,858,968 A | 1/1999 | Weiner et al. | 514/3 |
| 5,952,008 A | 9/1999 | Bäckström et al. | 424/499 |
| 5,997,848 A | 12/1999 | Patton et al. | 424/46 |
| 6,004,574 A | 12/1999 | Bäckström et al. | 424/434 |
| 6,051,256 A | 4/2000 | Platz et al. | 424/489 |
| 6,165,976 A | 12/2000 | Bäckström et al. | 514/3 |
| 6,306,440 B1 | 10/2001 | Bäckström et al. | 424/499 |
| 6,436,902 B1 | 8/2002 | Bäckström et al. | 514/12 |
| 6,524,557 B1 | 2/2003 | Bäckström et al. | 424/46 |
| 2003/0064928 A1 | 4/2003 | Bäckström et al. | 514/12 |

FOREIGN PATENT DOCUMENTS

| | | |
|---|---|---|
| GB | 1 527 605 | 4/1976 |
| GB | 1520247 | 8/1978 |
| GB | 1569611 | 6/1980 |
| JP | 632932 | 7/1988 |
| JP | Hei 4-41421 | 2/1992 |
| JP | Hei 47-149126 | 5/1992 |
| SE | 8 007 820-7 | 11/1917 |
| SE | 8007820-7 | 11/1986 |
| SE | 9 302 198-8 | 6/1993 |
| SE | 9 400 371-2 | 2/1994 |
| WO | WO 87/05213 A1 | 9/1987 |
| WO | WO 88/09163 | 1/1988 |
| WO | WO 90/07333 | 4/1990 |
| WO | 90/04962 | 5/1990 |
| WO | WO90/07333 | 7/1990 |
| WO | WO 91/16038 | 10/1991 |
| WO | 91/16882 | 11/1991 |
| WO | 91/16929 | 11/1991 |
| WO | WO 91/18091 A1 | 11/1991 |
| WO | WO 92/04069 | 3/1992 |
| WO | WO 92/06704 | 4/1992 |
| WO | WO92/08446 | 5/1992 |
| WO | WO 92/08446 | 5/1992 |
| WO | 93/25198 | 12/1993 |
| WO | 9407514 * | 4/1994 |
| WO | WO 94/07514 | 4/1994 |
| WO | 94/22461 | 10/1994 |
| WO | WO 95/00128 | 1/1995 |
| WO | 95/00151 | 1/1995 |
| WO | WO 96/19206 | 6/1996 |
| WO | WO 96/19207 | 6/1996 |
| WO | WO 97/10850 | 3/1997 |

OTHER PUBLICATIONS

Pifferi G (FARMACO 54 (1–2) 1–14, 1999).*
Barbaud A (Clinical Reviews in Allergy and Immunology 13 (3) 253–63, 1995).*
Byron et al., "Drug Delivery via the Respiratory . . . ," Journal of Aerosol Medicine, 7:49–75, 1994.
Nagano et al., "New Method of Insulin . . . ," Jikeikai Med. J., 32:503–506, 1985.
Elliott et al., "Parenteral absorption of insulin . . . ," Aust. Paediatr. J., 23:293–297, 1987.
Sakr., "A new approach for insulin . . . ," International Journal of Pharmaceutics, 86:1–7, 1992.
Liu et al., "Pulmonary Delivery of Free . . . ," Pharmaceutical Research, 10:228–232, 1993.
Remington's Pharmaceutical Science, 18th edn., p. 1079 (1990).
Longenecker et al., Effects of Sodium Taurodihydrofusidate on Nasal Absorption of Insulin in Sheep, *J. Pharm. Sci.,* 76(5):351–355 (1987).
Mizgala et al., Renal Handling of Phosphate, *Physiological Reviews,* 65(2):431–466 (1985).
Salzman et al., Intranasal Aerosolized Insulin Mixed–Meal Studies and Long–term Use in Type I Diabetes, *The New England Journal of Medicine,* 312:1078–1084, 1985.
Zingg et al., Transhepatic Absorption and Biliary Excretion of Insulin, *Can. J. Physiol. Pharmacol.,* 65:1982–1987 (1987).
Ruin, Sydsvenska (Dagbladet), Monday, Jun. 12, 1989, Diabetics May Not Need Their Insulin Shots.
Almer et al., Diabetes Res. and Clin. Pract. 5:s163 (1988).
Björk, Acta Univ. Uppsala, Comprehensive Summaries of Uppsala Dissertations from the Faculty of Pharmacy 103 (1993).
Timsina et al., Drug Delivery to the Respiratory Tract Using Dry Powder Inhalers, Int. J. Pharmaceutics 101:1–13 (1994).
Komada et al., Intratracheal Delivery of Peptide and Protein Agents: Absorption from Solution and Dry Powder by Rat Lung, J. Pharm. Sci. 83:863–867 (1994).
Lee et al., Intranasal Bioavailability of Insulin Powder Formulations: Effect of Permeation Enhancer–to–Protein Ratio, J. Pharm Sci. 80:725–729 (1991).
Schipper et al., Nasal Insulin Delivery with Dimethyl–β–Cyclodextrin as an Absorption Enhancer in Rabbits: Powder More Effective than Liquid Formulations, Pharm. Res. 10:682–686 (1993).
Lee et al., Mucosal Penetration Enhancers for Facilitation of Peptide and Protein Drug Absorption, Critical Rev. Therapeut. Drug Carrier Systems 8:91–192 (1991).
Wearley, Recent Progress in Protein and Peptide Delivery by Noninvasive Routes, Critical Rev. Therapeut. Drug Carrier Systems 8:331–394 (1991).
Laube et al., Preliminary Study of the Efficacy if Insulin Aerosol Delivered by Oral Inhalation in Diabetic Patients, JAMA 269:2106–2109 (1993).
Dahlbäck et al., Regional Administration of Drugs to the Rabbit Respiratory Tract, Effects on Absorption, J. Aersol Medicine 1:222–223 (1988).
Yoshida et al., Absorption of Insulin Delivered to Rabbit Trachea Using Aerosol Dosage Form, J. Pharma. Sci. 68:670–671 (1979).
Damasy et al., Diabetes Res. and Clin. Pract. 5:s163 (1988).
Chandler et al., Nasal Absorption in Rats. II. Effect of Enhancers on Insulin Absorption and Nasal Histology, Int. J. Pharmaceutics 76:61–70 (1991).
Hirai et al., Effect of Surfactants on the Nasal Absorption of Insulin in Rats, Int. J. Pharmaceutics 9:165–172 (1981).
Gordon et al., Nasal Absorption of Insulin: Enhancment by Hydrophobic Bile Salts, Proc. Natl. Acad. Sci. USA 82:7419–7423 (1985).
Moses et al., Insulin Administered Intranasally as an Insulin––Bile Salt Aerosol, Diabetes 32:1040–47 (1983).

Wigley et al., Insulin Across Respiratory Mucosae by Aerosol Delivery, Diabetes 20:552–556 (1971).

Cutie et al., The Role of Dispersing Agents in Inhalation and Intranasal Aerosol Suspensions, Aerosol. Age 30:52–54 (1985).

Goni et al., "Palmitoylcarnitine, a surface–active metabolite," FEBS Lett., vol. 390, pp. 1–5, 1996.

Jaegfeldt, H. et al., "Particle size distribution from different modifications of Turbuhaler," Proceedings of an international workshop on a new inhaler, May 21–22, 1987 (London) pp. 90–99.

Lecluyse et al., "In Vitro Effects of Long–Chain Acylcarnitines on the Permeability, Transepithelial Electrical Resistance and Morphology of Rat Colonic Mucosa," J. Pharmacol. Exp. Ther., vol. 265(2), pp. 955–962, 1993.

Okumura et al., "Intertracheal delivery of insulin absorption from solution ans aerosol by rat lung," International Journal of Pharmaceutics, vol. 88, pp. 63–73, 1992.

Yamamoto et al., "Absorption Enhancement of Intrapulmonary Administered Insulin by Various Absorption . . . ," J. Pharm. Pharmacol., vol. 46, pp. 14–18, 1994.

Allenby et al., The Absorption of Insulin Across the Respiratory Tract of the Guinea–Pig (U), The Aerosol Society, Fourth Annual Conference 1990, pp. 129–134.

Aungst and Rogers, Comparison of the Effects of Various Transmucosal Absorption Promoters on Buccal Insulin Delivery, Int. J. Pharm. (Netherlands), 1989, 53/3, 227–235.

Björk, Starch Microspheres as a Nasal Delivery System for Drugs, Comprehensive Summaries of Uppsala Dissertations from the Faculty of Pharmacy 103, 1993.

Björk and Edman, Degradable Starch Microspheres as a Nasal Delivery System for Insulin, Int. J. Pharm. 47:233–238, 1988.

Brange et al., Monomeric Insulins and Their Experimental and Clinical Imptications, Diabetes Care 13:923–954, 1990.

Edman and Björk, Routes of Delivery: Case Studies, Advanced Drug Delivery Reviews 8:165–177, 1992.

Igawa et al., Effect of Absorption Promoters in Intranasal Administration of Human Fibroblast Interferon as a Powder Dosage Form in Rabbits, Chem. Pharm. Bull. 37:418–421, 1989.

Komada et al., Intratracheal Delivery of Peptide and Protein Agents: Absorption from Solution and Dry Powder by Rat Lung, J. Pharm. Sci. 83:863–867, 1994.

Lasker, The Diabetes Control and Complications Trial, N. Engl. J. Med. 329:1035–1036, 1993.

Laube et al., Preliminary Study of the Efficacy of Insulin Aerosol Delivered by Oral Inhalation in Diabetic Patients, JAMA 269:2106–2109, 1993.

Lee et al., Intranasal Bioavailability of Insulin Powder Formulations: Effect of Permeation Enhancer–to–Protein Ratio, J. Pharm. Sci. 80:725–729, 1991.

Mishima et al., Studies on the Promoting Effects of Medium Chain Fatty Acid Salts on the Nasal Absorption of Insulin in Rats, J. Pharm –Dyn. 10:624–631, 1987.

Morita et al., Effects of Various Absorption Promoters on Pulmonary Absorption of Drugs with Different Molecular Weights, Biol. Pharm. Bull. 16:269:262, 1993.

Nagai et al., Powder Dosage Form of Insulin for Nasal Administration, J. Controlled Release 1:15–22, 1984.

"Diabetes Mellitus", Ch. VI in Scientific American Medicine, Scientific American, Inc., Apr. 1993.

The Diabetes Control and Complications Trial Research Group, The Effect of Intensive Treatment of Diabetes on the Development . . . Complications in Insulin–Dependent Diabetes Mellitus, N. Engl. J. Med. 329:977–86, 1993.

Pontiroli et al., Nasal Administration of Glucagon and Human Calcitonin to Healthy Subjects: a Comparison of Powders and Spray Solutions and of Different Enhancing Agents, Eur. J. Clin. Pharmacol. 37:427–430, 1989.

Schipper et al., Nasal Insulin Delivery with Dimethyl–β–Cyclodextrin as an Absorption Enhancer in Rabbits: Powder More Effective than Liquid Formulations, Pharmaceutical Research 10:682–686, 1993.

Selam and Charles, Devices for Insulin Administration, Diabetes Care 13:955–979, 1990.

Touitou and Rubenstein, Targeted Enteral Delivery of Insulin to Rats, Int. J. Pharm. (Amst.), 30(2–3), 1986, 95–100.

Wigley et al., Insulin Across Respiratory Mucosae by Aerosol Delivery, Diabetes 20:552–556, 1971.

Zinman, Medical Intelligence—The Physiologic Replacement of Insulin, N. Engl. J. Med. 321:363–370, 1989.

Chien et al., "Intranasal Drug Delivery For Systemic Medications", CRC Critical Reviews in Therapeutic Drug Carrier Systems 4:67–194, 1987.

Eppstein et al., "Alternative Delivery Systems for Peptides and Proteins As Drugs", CRC Critical Reviews in Therapeutic Drug Carrier Systems 5:99–139, 1988.

O'Hagan et al., "Absorption of Peptides and Proteins from the Respiratory Tract and the Potential for Development of Locally Administered Vaccine", Critical Reviews in Therapeutic Drug Carrier Sys 7:35–97, 1990.

Dempster et al., Anabolic Actions of Parathyroid Hormone on Bone, *Endocrine Reviews*, 14:690–709, (1993).

Patton et al., "Bioavailability of Pulmonary Delivered Peptides and Proteins: α–interferon, Calcitonins and Parathyroid Hormones," *Journal of Controlled Release*, 28: 79–85 (1994).

Schluter et al., "Pulmonary Adminstration . . . Type 1 Diabetics" Abstract #298, *Diabetes*, 33 (Supplement): 75A (1984).

Wang et al., *Parenteral Science and Technology*, 42 (2S), S4–S26, 1988.

Wetterlin, Kiell, "Turbuhaler: A New Powder Inhaler for Adminstration of Drugs to the Airways," *Pharmaceutical Research*, vol. 5, pp. 506–508, (1988).

Olanoff et al., "Method to Enhance Intranasal Peptide Delivery," in "Controlled–Release Technology Pharmaceutical Applications," Lee et al., American Chemical Society, 301–309, 1987.

Jacobs et al, "The Pharmacodynamics and . . . ," Diabetes, 42:1649–1655, 1993.

Aungst et al, "Comparison of Nasal . . . ," The Journal of Pharmacology and Experimental Therapeutics, 244:23–27, 1987.

Köhler et al., "Pulmonary Administration . . . ," Abstract 298, Diabetes 33 (Suppl.):75A, 1984.

Hoover et al, "Peptides are Better . . . ," Pharmaceutical Research, 9(8):1103–1106, 1992.

Colthorpe et al, "The Pharmacokinetics . . . ," Pharmaceutical Research, 9(6):pp. 764–768, 1992.

Chien et al, "Potential Development in . . . ," Drug Development and Industrial Pharmacy, 15(10):1601–1634, 1989.

Patton et al, "(D) Routes of Delivery: Case Studies," Advanced Drug Delivery Reviews, 8:179–196, 1992.

Li et al., "Effect of a . . . ,"60 Eur. J. Pharm. Biopharm., 39:216–221, 1993.

Salzman et al., "Intranasal Aerosolized . . . ," The New England Journal of Medicine, 312:1078–1084, 1985.

Bjork et al., "Characterization of degradable starch . . . ", Int. J. Pharmaceutics, 62 (1990) 187–192.

Jones, "Pulmonary Absorption of Insulin", (1998) Ph. D. Thesis, Welsh Schoot of Pharmacy, University of Wales, United Kingdom.

Lee et al., "Development of an Aerosol Dosage Form Containing Insulin", J. Pharmaceutical Sciences, vol. 65, No. 4,(1976) 567–574.

Newman, "Chapter 9: Therapeutic aerosols", In: Aerosols and the Lung: Clinical and Experimental Aspects, (1984) Butterworth & Co., United Kingdom.

Almar et al., Insulin Inhalation—At Last A Break–Through, Diabetes Res. Clin. Pract. 5:5163–POS–001–169, 1988.

Bjork, Starch Microspheres as a Nasal Delivery System for Drugs, ACTA Univ. Upsaliensis, UPPSALLA, Comprehensive Summaries of Uppsala Dissertations from the Faculty of Pharmacy, 103: parts 1–5, 1993.

Chandler et al., Nasal Absorption in Rats. II. Effect of Enhancers on Insulin Absorption and Nasal Histology, Int'l J. Pharmaceutics, 76:61–70, 1991.

Cutie et al., The Role of Dispersing Agents in Inhalation and Intrnasat Aerosol Suspensions, Aerosol Age, pp. 52–54, 1985.

Dahlback et al., Regional Adminstration of Drugs to the Rabbit Respiratory Tract, Effects on Absorption, J. Aerosol Medicine, 7th International Congress on Aerosols in Medicine, Sep. 1988, p. 222.

Dahlback et al., Deposition of Tracer Aerosols in the Rabbit Respiratory Tract, J. Aerosol Sci., vol. 18 No. 6, pp. 733–736, 1987.

Gordon et al., Nasal Absorption of Insulin: Enhancement by Hydrophobic Bite Salts, Proc. Nat'l Acad. Sci. USA, B2:7419–23, 1985.

Lee et al., Mucosal Penetration Enhancers for Facilitation of Peptide and Protein Drug Absorption, Critical Reviews in Therapeutic Drug Carrier Systems, 8(2):91–192, 1991.

Ruin, Diabetics May Not Need Their Insulin Shots, article in Sydsvenska (Dagbladet), Monday, Jun. 12, 1989. (English translation attached).

Schanker et al., Species Comparison of Drug Absorption from the Lung After Aerosol Inhalation or Intratracheal Injector, Drug Metabolism & Disposition, vol. 14, pp. 79–88, 1986.

Wearley, Recent Progress in Protein and Peptide Delivery by Noninvasive Routes, Critical Reviews in Therapeutic Drug Carrier Systems, 8(4):331–94, 1991.

Yoshida et al., Absorption of Insulin Delivered to Rabbit Trachea Using Aerosol Dosage Form, J. Pharm. Sci. 68:670, 1979.

English Abstract of Japanese Patent No. 1117825 A.

Köhler et al., "Aerosols for Systemic Treatment", Lung, Suppl. 677–684, 1990.

Translation of: Köhler et al., "Non radioactive procedure for the measurement if lung permeability: inhalation of insulin", Atemw.–Lungehkrkh., Jahrgang 13, Nr. Jun. 1987, S. 2309–232.

* cited by examiner

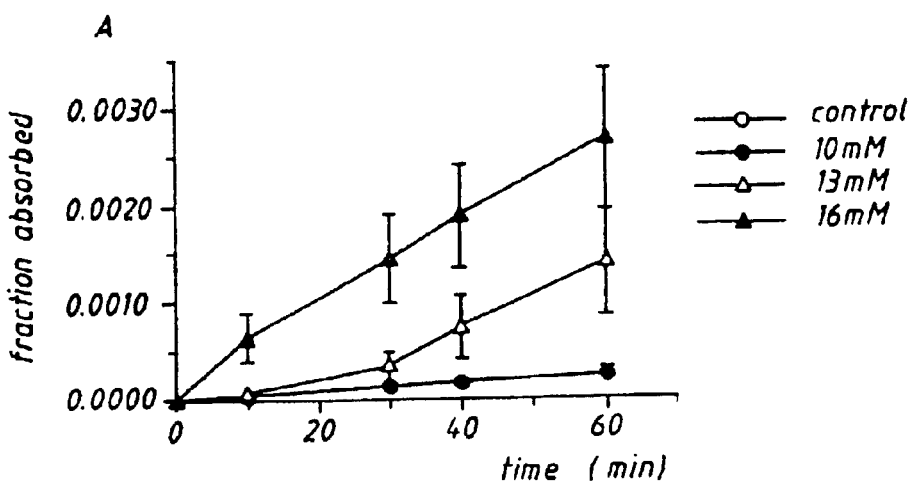
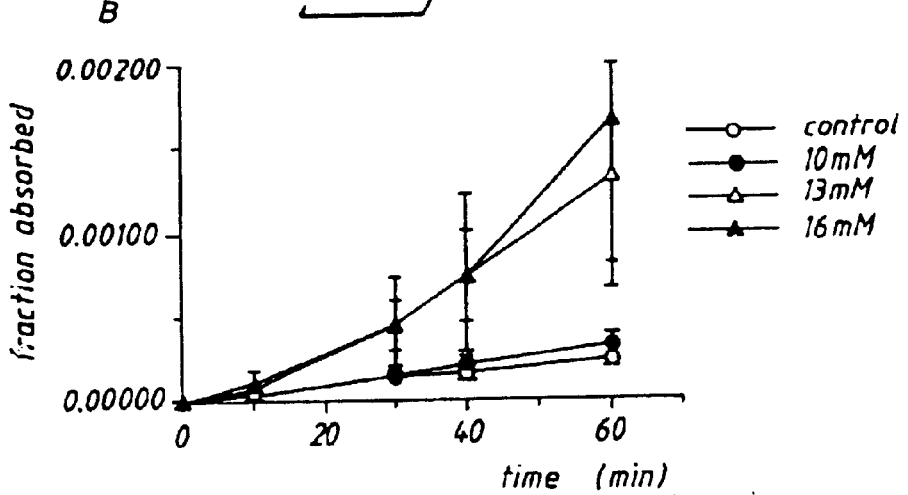
Transport of mannitol across Caco-2 cell monolayer in presence of Na-caprate (10-16mM)
A. Na-caprate
B. Na-caprate/insulin (1:3 w/w)

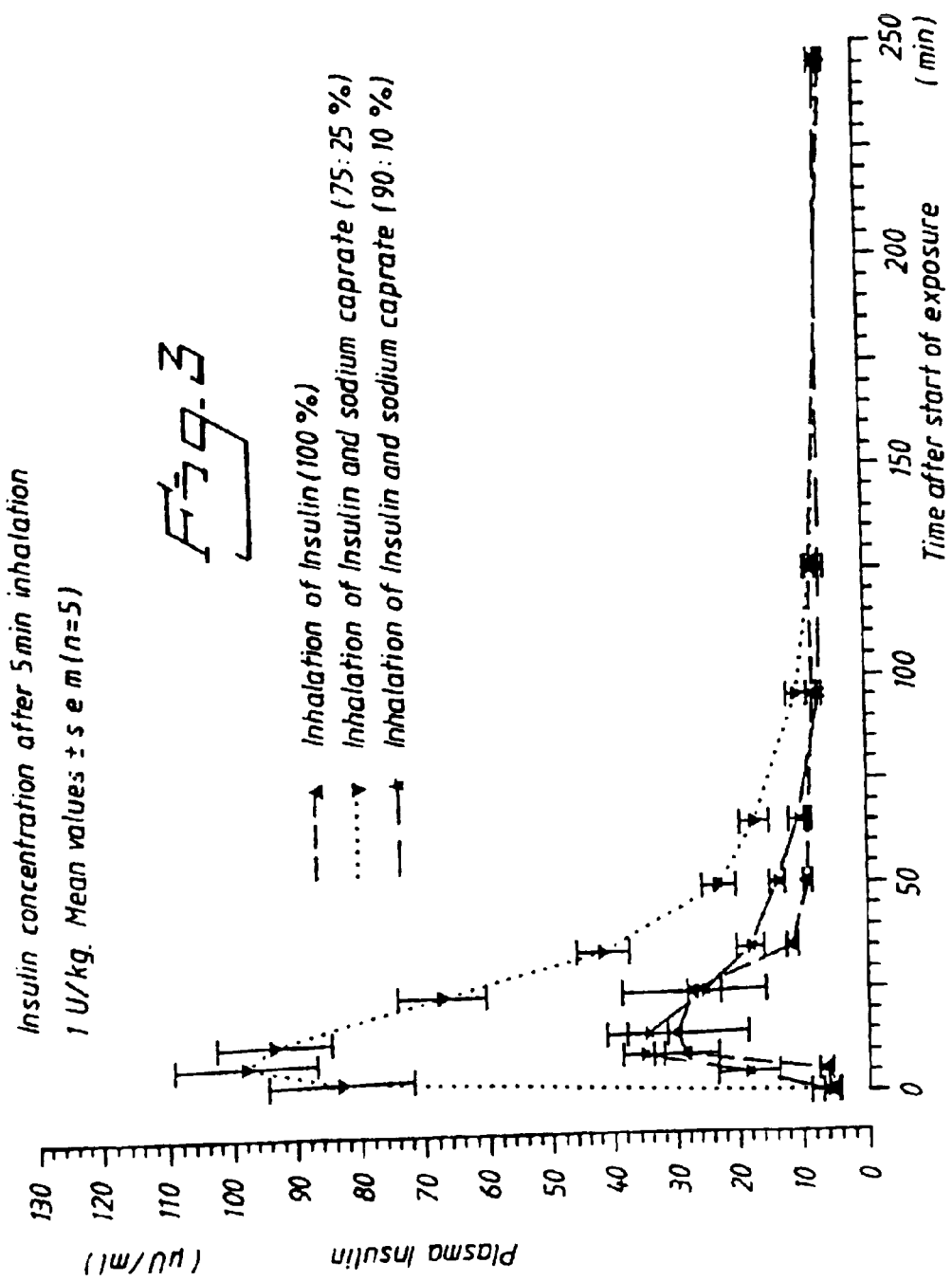

COMPOSITIONS FOR INHALATION this is a continuation of application Ser. No. 08/265,237, filed Jun. 23, 1994, now abandoned.

This invention relates to methods and compositions for delivery of medically useful peptides and proteins.

BACKGROUND OF THE INVENTION

Although the advent of recombinant DNA technology has resulted in a rapidly expanding list of peptide-based drugs, a major drawback of peptide-based therapy has acutely hampered realization of the full potential of this field: in general, peptide-based drugs cannot be orally administered in effective doses, since they are rapidly degraded by enzymes in the gastrointestinal tract before they can reach the bloodstream. Unless the polypeptide of interest can be altered to make it relatively resistant to such enzymes, the only practical method of delivering the drug is likely to be a parenteral route, such as by intravenous, intramuscular, or subcutaneous injection.

Administration by other parenteral routes (e.g., by absorption across nasal, buccal or rectal membranes, or via the lung) has met with limited success.

SUMMARY OF THE INVENTION

It has been found that when a peptide or protein (hereinafter collectively referred to as polypeptides) is combined with an appropriate absorption enhancer and is introduced into the lung in the form of a powder of appropriate particle size, it readily enters the pulmonary circulation by absorption through the layer of epithelial cells in the lower respiratory tract. This is conveniently accomplished by inhalation of the powder from an inhaler device which dispenses the correct dose of powdered polypeptide/ enhancer in a particle size which maximizes deposition in the lower respiratory tract, as opposed to the mouth and throat. (For ease of reference, the polypeptide and enhancer are hereinafter collectively referred to as the "active compounds"). To accomplish this preferential delivery into the lung, as much as possible of the active compounds should consist of particles having a diameter less than approximately 10 $\mu$m (e.g., between 0.01–10 am, and ideally between 1–6 $\mu$m). In preferred embodiments, at least 50% (preferably at least 60%, more preferably at least 70%, still more preferably at least 80%, and most preferably at least 90%) of the total mass of active compounds which exits the inhaler device consists of particles within the desired diameter range.

The invention thus includes a pharmaceutical composition containing a mixture of active compounds (A) a pharmaceutically active polypeptide and (B) an enhancer compound which enhances the systemic absorption of the polypeptide in the lower respiratory system (preferably the lungs) of a patient, the mixture being in the form of a dry powder suitable for inhalation, in which at least 50% of the total mass of active compounds (A) and (B) consists of primary particles having a diameter less than or equal to about 10 microns. The primary particles may be packaged as such, or may optionally be formed into agglomerates, which then are substantially deagglomerated prior to entry into the respiratory tract of the patient. The composition may of course contain other ingredients as needed, including other pharmaceutically active agents, other enhancers, and pharmacologically acceptable excipients such as diluents or carriers. Therefore, the therapeutic preparation of the present invention may contain only the said active compounds or it may contain other substances, such as a pharmaceutically acceptable carrier. This carrier may largely consist of-particles having a diameter of less than about 10 microns so that at least 50% of the resultant powder as a whole consists of optionally agglomerated primary particles having a diameter of less than about 10 microns; alternatively the carrier may largely consist of much bigger particles ("coarse particles"), so that an "ordered mixture" may be formed between the active compounds and the said carrier. In an ordered mixture, alternatively known as an interactive or adhesive mixture, fine drug particles (in this invention, the active compounds) are fairly evenly distributed over the surface of coarse excipient particles (in this invention, the pharmaceutically acceptable carrier). Preferably in such case the active compounds are not in the form of agglomerates prior to formation of the ordered mixture. The coarse particles may have a diameter of over 20 microns, such as over 60 microns. Above these lower limits, the diameter of the coarse particles is not of critical importance so various coarse particle sizes may be used, if desired according to the practical requirements of the particular formulation. There is no requirement for the coarse particles in the ordered mixture to be of the same size, but the coarse particles may advantageously be of similar size within the ordered mixture. Preferably, the coarse particles have a diameter of 60–800 microns.

The polypeptide may be any medically or diagnostically useful peptide or protein of small to medium size, i.e. up to about 40 kD molecular weight (MW), for which systemic delivery is desired. The mechanisms of improved polypeptide absorption according to the present invention are generally applicable and should apply to all such polypeptides, although the degree to which their absorption is improved may vary according to the MW and the physico-chemical properties of the polypeptide, and the particular enhancer used. It is expected that polypeptides having a molecular weight of up to 30 kD will be most useful in the present invention, such as polypeptides having a molecular weight of up to 25 kD or up to 20 kD, and especially up to 15 kD or up to 10 kD. Any desired polypeptide may be easily tested for use in the present invention with a particular enhancer, by in vivo or in vitro assays, as described herein.

The enhancer compound used in the compositions of the present invention can be any compound which enhances the absorption of the polypeptide through the epithelium of the lower respiratory tract, and into the systemic circulation. By "enhances absorption" is meant that the amount of polypeptide absorbed into the systemic circulation in the presence of enhancer is higher than in the absence of enhancer. Preferably the amount of polypeptide absorbed is significantly higher ($p<0.05$) in the presence of enhancer. The suitability of any potential enhancer for use in the present invention may be easily assessed, by means of in vivo or In vitro assays, as described herein.

The amount of polypeptide absorbed according to the present invention is preferably at least 150% of the amount absorbed in the absence of enhancer. In preferred embodiments, absorption of polypeptide is at least doubled, more preferably tripled, and most preferably quadrupled in the presence of the enhancer, compared to in its absence.

The enhancer is preferably a surfactant such as a salt of a fatty acid, a bile salt, a bile salt derivative, an alkyl glycoside, a cyclodextrin, or a phospholipid. The enhancer may be, for example, a sodium, potassium, or organic amine salt of the fatty acid, and the fatty acid is preferably capric acid or another fatty acid of 10–14 carbon atoms. The preferred enhancer is sodium caprate. The ratio of polypeptide to enhancer will preferably vary from about 9:1 to about 1:1. Although proportions of enhancer greater than 1:1 would presumably enhance uptake as well as or better than lower proportions, it is believed that the amount of enhancer used should be no higher than necessary to acheive the desired level of enhancement, since excess enhancer may trigger unwanted side effects, such as local irritation.

Also within the invention is a method of administering systemically a pharmaceutically active polypeptide, by causing a patient to inhale the pharmaceutical composition of the invention, wherein at least 50% of the total mass of the active compounds at the point of entry to the respiratory tract of the patient consists of particles having a diameter less than or equal to about 10 microns. This is preferably accomplished by the use of an inhaler device from which the patient inhales the powder. Where the powdered composition is in the form of agglomerates of primary particles, the device is preferably configured to induce substantial deagglomeration of the agglomerates upon inhalation of the powder from the device by the patient, so that the majority of the agglomerates break down into particles having a diameter less than or equal to about 10 microns, prior to entry of the powder into the respiratory system of the patient. This deagglomeration would occur inside the device, and is typically induced by the air turbulence created in the device by the force of inhalation. Agglomerates are in general preferably not formed in the ordered mixture. In the case of an ordered mixture, the active compounds should be released from the large particles preferably upon inhalation, either by mechanical means in the inhaler device or simply by the action of inhalation, or by other means, the active compounds then being deposited in the lower respiratory tract and the carrier particles in the mouth.

The inhaler device is preferably a single dose dry powder inhaler, but may alternatively be a multi dose dry powder inhaler.

The invention also includes processes for the manufacture of a pharmaceutical composition suitable for administration by inhalation. In one such process, a solution is first provided in which are dissolved (a) a pharmaceutically active polypeptide and (b) an enhancer compound which enhances the systemic absorption of the polypeptide in the lower respiratory tract of a patient. The solvent is then removed from the solution to yield a dry solid containing the polypeptide and the enhancer, and the dry solid is pulverized to produce a powder. A second such process involves dry mixing (a) a pharmaceutically active polypeptide and (b) an enhancer compound, and micronizing the obtained mixture. Yet a third suitable process includes the steps of providing a first micronized preparation containing a polypeptide and a second micronized preparation containing an enhancer compound, and mixing the two micronized preparations together. When a carrier is to be included other than when an ordered mixture is desired, this may be added to the solution, or to the dry-mixture of the pharmaceutically active polypeptide prior to micronization, or micronised carrier may be dry mixed with the other micronised components. In producing an ordered mixture, micronised polypeptide and enhancer are mixed with a suitable carrier.

BRIEF DESCRIPTION OF THE DRAWINGS

FIG. 1 is a graph illustrating the effects of different concentrations of sodium caprate enhancer on the transport of a marker compound (mannitol) through a monolayer of cultured epithelial cells.

FIG. 2 is a graph illustrating the effects of different concentrations of sodium caprate enhancer on the transport of a marker compound (mannitol) through a monolayer of cultured epithelial cells, in the presence of a polypeptide (sodium caprate:polypeptide 1:3 by weight).

FIG. 3 is a graph of plasma polypeptide concentration as a function of time after inhalation of the polypeptide alone, the polypeptide with sodium caprate in a ratio of 90:10, and the polypeptide with sodium caprate in a ratio of 75:25.

DETAILED DESCRIPTION

Some of the preferred embodiments of the invention are generally described below.

The Polypeptide

The polypeptide is preferably a peptide hormone other than insulin, such as vasopressin, vasopressin analoques, desmopressin, glucagon, corticotropin (ACTH), gonadotrophin (luteinizing hormone, or LHRH), calcitonin, C-peptide of insulin, parathyroid hormone (PTH), human growth hormone (hGH), growth hormone (HG), growth hormone releasing hormone (GHRH), oxytocin, corticotropin releasing hormone (CRH), somatostatin analogs, gonadotropin agonist analogs (GnRHa), human gatrial natriuretic peptide (hANP) recombinant human thyroxine releasing hormone (TRHrh), follicle stimulating hormone (FSH), and prolactin.

Other possible polypeptides include growth factors, interleukins, polypeptide vaccines, enzymes, endorphins, glycoproteins, lipoproteins, and polypeptides involved in the blood coagulation cascade, that exert their pharmacological effect systemically. It is expected that most if not all polypeptides of small to medium size, relatively high water solubility, and an isoelectric point between approximately pH 3 and pH 8 can be effectively delivered by the methods of the invention.

The Enhancer

The use of an absorption enhancer is of critical importance, as the polypeptide alone is poorly absorbed through the lung. The enhancer used can be any of a number of compounds which act to enhance absorption through the layer of epithelial cells lining the lower respiratory tract, and into the adjacent pulmonary vasculature. The enhancer can accomplish this by any of several possible mechanisms:

(1) Enhancement of the paracellular permeability of a polypeptide by inducing structural changes in the tight junctions between the epithelial cells.

(2) Enhancement of the transcellular permeability of a polypeptide by interacting with or extracting protein or lipid constituents of the membrane, and thereby perturbing the membrane's integrity.

(3) Interaction between enhancer and polypeptide which increases the solubility of the polypeptide in aqueous solution. This may occur by preventing formation of insulin aggregates (dimers, trimers, hexamers), or by solubilizing polypeptide molecules in enhancer micelles.

(4) Decreasing the viscosity of, or dissolving, the mucus barrier lining the alveoli and passages of the lung, thereby exposing the epithelial surface for direct absorption of the polypeptide.

Enhancers may function by only a single mechanism set forth above, or by two or more. An enhancer which acts by several mechanisms is more likely to promote efficient absorption of a polypeptide than one which employs only one or two.

For example, surfactants are a class of enhancers which are believed to act by all four mechanisms listed above. Surfactants are amphiphilic molecules having both a lipophilic and a hydrophilic moiety, with varying balance between these two characteristics. If the molecule is very lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity.

Another surfactant property that may be of importance is the net charge of the surfactant at the pH value in the lung (approximately 7.4). At pH 7.4, some polypeptides have a negative net charge. This will result in an electrostatic repulsion between molecules, which will in turn prevent aggregation and thereby increase the solubility. If the surfactant also is negatively charged, it can interact with the polypeptide by, for example, hydrophobic interactions, and additional repulsion among the polypeptide molecules will occur. In such case an anionic surfactant will possess the additional advantage (compared to those having neutral or net positive charge at physiological pH) of enhancing absorption by helping stabilize the polypeptide in the monomeric state.

A number of different compounds potentially useful as enhancers in the methods of the invention were tested in rats, as described in Example 2 below. Other substances with known absorption-enhancing properties, or with physical characteristics which make them likely candidates for use in the method of the invention, can be readily tested by one of ordinary skill in that in vivo assay, or alternatively in the in vitro assay described in Example 1.

It is possible that a combination of two or more enhancer substances also gives satisfactory results. The use of such a combination in the method of the invention is considered to be within the invention.

An enhancer useful in the methods of the invention will combine effective enhancement of polypeptide absorption with (1) lack of toxicity in the concentrations used and (2) good powder properties, i.e., lack of a sticky or waxy consistency in the solid state. Toxicity of a given substance can be tested by standard means, such as by the MTT assay, for example as described in Int. J. Pharm., 65 (1990), 249–259. The powder properties of a given substance may be ascertained from published data on the substance, or empirically.

One very promising type of enhancer is the salt of a fatty acid. It has been found that the sodium salt of saturated fatty acids of carbon chain length 10 (i.e., sodium caprate), 12 (sodium laurate) and 14 (sodium myristate) perform well in the method of the invention. The potassium and lysine salts of capric acid have also been found to be effective in the method of the invention. If the carbon chain length is shorter than about 10, the surface activity of the surfactant may be too low, and if the chain length is longer than about 14, decreased solubility of the fatty acid salt in water limits its usefulness.

Most preferably in the present invention the substance which enhances the absorption of polypeptide in the lower respiratory tract is sodium caprate.

Different counterions may change the solubility of the saturated fatty acid salt in water, such that an enhancer having a carbon length other than 10–14 would prove even more advantageous than the enhancers specifically mentioned hereinabove. Salts of unsaturated fatty acids may also be useful in the present invention since they are more water soluble than salts of saturated fatty acids, and can therefore have a longer chain length than the latter and still maintain the solubility necessary for a successful enhancer of polypeptide absorption.

All of the bile salts and bile salt derivatives tested (sodium salts of ursodeoxycholate, taurocholate, glycocholate, and taurodihydrofusidate) effectively enhance polypeptide absorption in the lung.

Phospholipids were also tested as enhancers. It was found that a single-chain phospholipid (lysophosphatidylcholine) was an effective enhancer, while one double-chain phospholipid (didecanoylphosphatidylcholine) was not. This may be explained by the fact that the double-chain phospholipid is much less soluble in water than its single-chain counterpart; however, it is reasonable to expect that double-chain phospholipids of shorter chain length, having greater water solubility than their longer chain counterparts, will be of use as enhancers in the present invention so that both single- and double-chain phospholipids may be One glycoside, octylglucopyranoside, was tested as an enhancer in the present invention and was found to have some absorption enhancing properties. Other alkyl glycosides, such as thioglucopyranosides and maltopyranosides would also be expected to exhibit absorption enhancing properties in the methods of the present invention.

The cyclodextrins and derivatives thereof effectively enhance nasal absorption, and may function similarly in the lung. Dimethyl-β-cyclodextrin has been tested and was found to have an absorption enhancing effect.

Other potentially useful surfactants are sodium salicylate, sodium 5-methoxysalicylate, and the naturally occurring surfactants such as salts of glycyrrhizine acid, saponin glycosides and acyl carnitines.

For ionic enhancers (e.g., the anionic surfactants described above), the nature of the counterion may be important. The particular counterion selected may influence the powder properties, solubility, stability, hygroscopicity, and local/systemic toxicity of the enhancer or of any formulation containing the enhancer. It may also affect the stability and/or solubility of the polypeptide with which it is combined. In general, it is expected that monovalent metallic cations such as sodium, potassium, lithium, rubidium, and cesium will be useful as counterions for anionic enhancers. Ammonia and organic amines form another class of cations that is expected to be appropriate for use with anionic enhancers having a carboxylic acid moiety. Examples of such organic amines include ethanolamine, diethanolamine, triethanolamine, 2-amino-2-methylethylamine, betaines, ethylenediamine, N,N-dibensylethylenetetraamine, arginine, hexamethylenetetraamine, histidine, N-methylpiperidine, lysine, piperazine, spermidine, spermine and tris (hydroxymethyl)aminomethane.

Since effective enhancement of polypeptide absorption in the lung was observed for a number of the enhancers tested, it is expected that many more will be found which also function in this manner. Starch microspheres effectively enhance the bioavailability of polypeptide delivered via the nasal membranes and were tested as an enhancer in the methods of the invention. Although they proved to be of little use for delivery via the pulmonary route in the animal model utilized herein, it is thought that this was mainly due to technical difficulties which, if overcome, may lead to successful delivery via the pulmonary route.

Chelators are a class of enhancers that are believed to act by binding calcium ions. Since calcium ions help maintain the dimensions of the space between cells and additionally reduce the solubility of a polypeptide, binding of these ions would in theory both increase the solubility of polypeptides, and increase the paracellular permeability of polypeptides. Although one chelator tested, the sodium salt of ethylenediaminetetraacetic acid (EDTA), was found to be ineffective in enhancing absorption of insulin in the rat model tested, other calcium ion-binding chelating agents may prove to be more useful.

Proportions of Polypeptide and Enhancer The relative proportions of polypeptide and enhancer may be varied as desired. Sufficient enhancer must be present to permit efficient absorption of the inhaled polypeptide; however, the amount of enhancer should be kept as low as possible in order to minimize the risk of adverse effects caused by the enhancer. Although each particular polypeptide/enhancer combination must be tested to determine the optimal proportions, it is expected that to achieve acceptable absorption of the polypeptide, more than 10% of the polypeptide/enhancer mixture must be enhancer; for most types of enhancers, the proportion of enhancer should be more than 15% or more than 20% and will preferably be between 25% and 50%. The preferred ratio for each polypeptide/enhancer (or polypeptide/enhancer/diluent) combination can be readily determined by one of ordinary skill in the art of pharmacology by standard methods, based on such criteria as efficient, consistent delivery of the optimal dosage, minimization of side effects, and acceptable rate of absorption.

No further ingredients are needed for the action of the preparation, but may be included if desired. For example, the amount of powder which constitutes a single dose of a given polypeptide/surfactant combination could be increased (e.g., for use in an inhaler apparatus which by design requires a large powder volume per dose) by diluting the powder with pharmaceutically acceptable diluents. Other additives may be included to facilitate processing or to improve the powder properties or stability of the preparation. A flavouring agent could be added so that the proportion of the powder which is inevitably deposited in the mouth and throat would serve to give the patient positive feedback that a dose had been delivered from the inhaler device. Any such additive should have the following properties: (a) it is stable and does not disadvantageously affect the stability of the polypeptide and enhancer; (b) it does not disadvantageously interfere with absorption of the polypeptide; (c) it has good powder properties, as that term is understood in the pharmaceutical arts; (d) it is not hygroscopic; and (e) it has no adverse effects in the airways in the concentrations used. Useful types of such additives include mono-, di-, and polysaccharides, sugar alcohols, and other polyols: for example, lactose, glucose, raffinose, melezitose, lactitol, maltitol, trehalose, sucrose, mannitol, and starch. As reducing sugars such as lactose and glucose have a tendency to form complexes with proteins, non-reducing sugars such as raffinose, melezitose, lactitol, maltitol, trehalose, sucrose, mannitol and starch may be preferred additives for use in the present invention. Such additives may constitute anywhere from 0% (i.e., no additive) to nearly 100% of the total preparation.

In a preferred embodiment, this invention provides a therapeutic preparation of a pharmaceutically active polypeptide and a substance which enhances the absorption of said polypeptide in the lower respiratory tract, which preparation is in the form of a dry powder preparation suitable for inhalation of which at least 50% by mass consists of (a) particles having a diameter of less than about 10 microns or (b) agglomerates of said particles; in another preferred embodiment, the invention provides a therapeutic preparation comprising a pharmaceutically active polypeptide, a substance which enhances the absorption of polypeptide in the lower respiratory tract, and a pharmaceutically acceptable carrier, which preparation is in the form of a dry powder suitable for inhalation of which at least 50% by mass consists of (a) particles having a diameter of less than about 10 microns, or (b) agglomerates of said particles; and in a further preferred embodiment this invention provides a therapeutic preparation comprising active compounds (A) a pharmaceutically active polypeptide and (B) a substance which enhances the absorption of said polypeptide in the lower respiratory tract, wherein at least 50% of the total mass of active compounds (A) and (B) consists of particles having a diameter of less than about 10 microns, and a pharmaceutically acceptable carrier, which preparation is in the form of a dry powder preparation suitable for inhalation in which an ordered mixture may be formed between the active compounds and the pharmaceutically acceptable carrier.

The described powder preparation could be manufactured in several ways, using conventional techniques. In many cases, the purified polypeptide can be obtained from commercial sources. Alternatively, the polypeptide of interest can be purified from a naturally occurring source using standard biochemical techniques, or can be obtained by expression of prokaryotic or eukaryotic cells genetically engineered to contain a nucleotide sequence which encodes the polypeptide and has appropriate expression control sequences linked thereto (including a transgenic animal engineered to manufacture the desired peptide or protein, for example in its milk). Such methods are standard in the art (e.g., see Sambrook et al., Molecular Cloning: A Laboratory Manual; Cold Spring Harbor Laboratory Press, Cold Spring Harbor, N.Y., 1989). Peptides (i.e., polypeptides having 30 or fewer amino acid residues) can be readily synthesized by known chemical means.

Absorption enhancers as described above are also generally available from commercial sources, or can be manufactured using published methods. For ionic enhancers, the counterion associated with the enhancer can be replaced with another, if desired, using standard ion exchange techniques.

In manufacturing of the described powder preparation it will in general be necessary to micronize the powder in a suitable mill, e.g. a jet mill, at some point in the process, in order to produce primary particles in a size range appropriate for maximal deposition in the lower respiratory tract (i.e., under 10 $\mu$m). For example, one can dry mix polypeptide and enhancer powders, and then micronize the substances together; alternatively, the substances can be micronized separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible first to dissolve the components in a suitable solvent, e.g. water, to obtain mixing on the molecular level. This procedure also makes it possible to adjust the pH-value to a desired level, for instance to improve absorption of the polypeptide. The pharmaceutically accepted limits of pH 3.0 to 8.5 for inhalation products must be taken into account, since products with a pH outside these limits may induce irritation and constriction of the airways. To obtain a powder, the solvent must be removed by a process which retains the polypeptide's biological activity. Suitable drying methods include vacuum concentration, open drying, spray drying, and freeze drying. Temperatures over 40° C. for more than a few minutes should generally be avoided, as some degradation of certain polypeptides may occur. Following the drying step, the solid material can, if necessary, be ground to obtain a coarse powder, then, if necessary, micronized.

If desired, the micronized powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range. Where an ordered mixture is desired, the active compound may be processed, for example by micronisation, in order to obtain, if desired, particles within a particular size range. The carrier may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfills the said requirements, and may be determined easily by the skilled person according to the particular circumstances.

A preferred inhalation apparatus would have the following design characteristics: protection of the powder from moisture and no risk of occasional large doses; in addition as many as possible of the following are desired:

protection of the powder from light; high respirable fraction and high lung deposition in a broad flow rate interval; low deviation of dose and respirable fraction; low retention of powder in the mouthpiece—this is particularly important for a multidose inhaler, where polypeptide retained in the mouthpiece could degrade and then be inhaled together with subsequent doses; low adsorption to the inhaler surfaces; flexibility in dose size; and low inhalation resistance. The inhaler is preferably a single dose inhaler although a multi dose inhaler, such as a multi dose, breath actuated, dry powder inhaler for multiple use, may also be employed. Peferably the inhaler used is a unit dose, breath actuated, dry powder inhaler for single use.

A number of dry powder formulations containing a polypeptide and various enhancers have been prepared and tested in an in vivo assay, and are described below. Also described is an in vitro assay useful for testing polypeptide/enhancer combinations.

EXAMPLE 1

In Vitro Method of Determining Usefulness of Particular Polypeptides for the Present Invention A standard in vitro assay utilizing an epithelial cell line, CaCo-2 (available through the American Type Culture Collection (ATCC), Rockville, Md., USA), has been developed to assess the ability of various enhancer compounds to promote transport of markers across an epithelial cell monolayer, as a model for the epithelial cell layer which functions in the lung to separate the alveolus from the pulmonary blood supply.

In this assay, the enhancer and polypeptide or other marker are dissolved in aqueous solution at various proportions and/or concentrations, and applied to the apical side of the cell monolayer. After 60 min incubation at 37° C. and 95% RH (relative humidity), the amount of the marker on the basolateral side of the cells is determined, e.g., by use of a radioactively labelled marker.

For the enhancer tested, sodium caprate, the amount of marker (mannitol, MW 360) which appears on the basolateral side is dependent upon the concentration of enhancer used, at least up to 16 mM sodium caprate (FIG. 1). This is true even when the polypeptide insulin is added to the enhancer/mannitol mixture (1:3 sodium caprate:insulin, by weight) (FIG. 2). This concentration of sodium caprate (16 mM) was also found to promote absorption across the cell monolayer of two low molecular weight peptides, insulin (MW 5734) and vasopressin (MW 1208). The amount of insulin which passed across the monolayer doubled in the presence of 16 mM sodium caprate, compared to the amount in the absence of any enhancer; the amount of vasopressin which was absorbed across the monolayer increased 10–15 times compared to the amount in the absence of any enhancer.

In contrast, no increase in transport rate was observed for larger proteins such as cytochrome C (MW 12,300), carbonic anhydrase (MW 30,000) and albumin (MW 69,000) when tested at up to 16 mM sodium caprate. It is expected that at higher concentrations of sodium caprate, the permeability of the cells will be further increased, permitting the transport of larger polypeptides; however, the potential cytotoxicity of sodium caprate may prevent the use of substantially higher concentrations of this particular enhancer.

Other enhancers may permit transportation of larger polypeptides; these may also be tested in this in vitro model of epithelial cell permeability, which can be used as a screening tool for rapidly testing any desired polypeptide/enhancer combination for usefulness in the methods of the invention.

EXAMPLE 2

Method for Selecting Enhancers Useful for the Present Invention,

Each of the compounds listed in Table I was tested for its ability to enhance uptake of a polypeptide (insulin) in a rat model. The results with insulin are taken as indicative of the enhancer's potential for enhancement of absorption of other polypeptides.

Various forms of insulin were employed in the different trials: recombinant human, semisynthetic human or bovine. Each formulation was prepared as above, drying and processing the insulin/enhancer or insulin/enhancer/lactose solution to produce an inhalable powder. The powder was administered to rats by inhalation, and the blood glucose levels of the rats were subsequently monitored as a measure of insulin uptake. These levels were compared to the corresponding values obtained from rats which had inhaled insulin formulations without enhancer.

The same in vivo model system could be used to test any given peptide or protein for usefulness in the methods of the invention, by delivering by the same inhalation method a formulation containing the desired peptide or protein combined with an enhancer, and assaying for the concentration of the desired peptide or protein in the systemic circulation of the test animal (e.g., by standard immunoassays or biochemical assays as appropriate for the given peptide or protein).

TABLE I

| Substance | Enhancer: Insulin: lactose | Effect |
|---|---|---|
| Octylglucopyranoside | 4:4:92 | (+) |
| Sodium ursodeoxycholate | 4:4:92 | + |

TABLE I-continued

| Substance | Enhancer:Insulin:lactose | Effect |
|---|---|---|
| Sodium taurocholate | 4:4:92 | + |
| Sodium glycocholate | 4:4:92 | + |
| Lysophosphatidylcholine | 4:4:92 | + |
| Dioctanoylphosphatidylcholine | 2:4:94 | (+) |
| Didecanoylphosphatidylcholine | 4:4:94 | – |
| Sodium taurodihydrofusidate | 2:4:94 | + |
| Sodium caprylate | 25:75:0 | – |
| Sodium caprate | 10:90:0 | (+) |
| Sodium caprate | 17.5:82.5:0 | (+) |
| Sodium caprate | 25:75:0 | + |
| Potassium oleate | 4:4:92 | + |
| Sodium laurate | 25:75:0 | + |
| Potassium oleate | 4:4:92 | + |
| Potassium caprate | 27:73:0 | + |
| Lysine caprate | 35:65:0 | + |
| Sodium myristate | 30:70:0 | + |
| Dimethyl-β-cyclodextrin | 75:25:0 | + |

+ effect, i.e. enhancer gives a significant decrease in blood glucose level
– no or very small effect
(+) effect, not as marked as "+"

EXAMPLE 3

Therapeutic Preparation According to the Invention

Human growth hormone (hGH, MW 22 kD, source Humatrope from Lilly, 3 parts) was mixed with sodium caprate (1 part). The mixture was milled in a Retsch mechanical mill to a particle size of mass median diameter 6.7 μm.

The resultant powder was administered intratraceally in rats and the uptake of hGH compared with that of a powder, MMD 9.6 μm, comprising hGH and mannitol in the same proportions and prepared in the same way as above.

The results indicated an improvement in the uptake of hGH in the formulation including sodium caprate, compared with the uptake in the formulation without enhancer.

EXAMPLE 4

Preparation Containing the Polypeptide Insulin

Insulin is herein used as indicative of other polypeptides according to the present invention.

Biosynthetic human insulin (53 g) was micronised in an Airfilco Jet Mill (Trade Mark, Airfilco Process Plant Limited), with pressurised nitrogen (feed pressure 7 bar, chamber pressure 5 bar), to a mass median diameter of 2.4 micrometers.

Sodium caprate (170 g) was micronised in an Airfilco Jet Mill (TM), with pressurised nitrogen (feed pressure 5 bar, chamber pressure 3 bar), to a mass median diameter of 1.6 micrometers.

The micronised biosynthetic human insulin (45 g) and sodium caprate (14.26 g) were dry mixed according to the following procedure: Half of the insulin was added to a mixing device comprising a mixing cylinder of volume 4.4 litres divided, by a sieve of width 1 mm, into two compartments, with a metal ring in each compartment to aid mixing and stirring. The sodium caprate and finally the rest of the insulin, were added. The mixing cylinder was closed, turned 180 degrees, and mounted in a motorised shaking apparatus. The motor was turned on and shaking continued for approximately two minutes, until all the insulin and sodium caprate had passed through the sieve. The motor was turned off and the mixing cylinder turned 180 degrees, again mounted on the shaking apparatus and shaking was again effected until all the powder had passed through the sieve. This procedure was repeated a further eight times to give a total mixing time of approximately 20 minutes.

The preparation so obtained was administered to 5 dogs by inhalation, at a dosage level of 1 U./kg, and the plasma insulin level determined at various time points after administration.

The results obtained were compared with the plasma insulin levels obtained when biosynthetic insulin, micronised as above to a mass median diameter of 2.4 micrometers, were administered to five dogs in the same way and at the same dosage levels, and with the plasma insulin levels obtained when a therapeutic preparation of insulin and sodium caprate in a ratio of 90:10 was administered to five dogs in the same way and at the same dosage levels as above. In this case the therapeutic preparation was prepared as follows: Human semisynthetic insulin was gel filtrated to reduce the zinc content from 0.52% to 0.01% relative to content of insulin. Insulin (4.5 g) and sodium caprate (0.5 g) were dissolved in water (232 ml). The solution was stirred until clear and the pH adjusted to 7.0. The solution was concentrated by evaporation at 37° C. over a period of about two days. The obtained solid cake was crushed, and sieved through a 0.5 mm sieve, and the resultant powder micronised through a jet mill to particles with a mass median diameter of 3.1 micrometers.

The results of these comparisons are presented in FIG. 3 (p=0.0147 for the difference between 75:25 and 100:0). The results demonstrate some improvement in the bioavailability of insulin with the 90:10 formulation, and a dramatic improvement in the bioavailability of insulin with the 75:25 preparation including sodium caprate, as compared to insulin alone.

What is claimed is:

1. A propellant-free composition consisting of (A) a polypeptide, and (B) one or more surfactant compounds which (i) have a consistency that permits them to be processed into primary particles having a diameter less than 10 microns, and (ii) enhance the systemic absorption of said polypeptide in the lower respiratory tract of a patient, said composition being in the form of a dry powder suitable for inhalation from a dry powder inhaler device, wherein at least 50% of the total mass of (A) and (B) consists of primary particles having a diameter less than 10 microns or equal to about 10 microns, and wherein each of the one or more surfactant compounds is selected from the group consisting of a salt of a fatty acid, bile salt, single-chain phospholipid, double-chain phospholipid in which each chain of the double-chain phospholipid is eight or fewer carbon atoms in length, alkyl glycoside, cyclodextrin or derivative thereof, salt of a glycyrrhizine acid, salt of a saponin glycoside, salt of an acyl carnitine, and sodium salicylate.

2. The composition of claim 1, wherein said polypeptide is a polypeptide hormone.

3. The composition of claim 2, wherein said hormone is vasopressin, desmopressin, glucagon, corticotropin (ACTH), gonadotropin (luteinizing hormone, or LHRH), calcitonin, C-peptide of insulin, parathyroid hormone (PTH), human growth hormone (hGH), growth hormone (HG), growth hormone releasing hormone (GHRH), oxytocin, corticotropin releasing hormone (CRH), somatostatin, gonadotropin agonist, human atrial natriuretic peptide (hANP), recombinant human thyroxine releasing hormone (TRHrh), follicle stimulating hormone (FSH), or prolactin.

4. The composition of claim 1, wherein said polypeptide is a growth factor, interleukin, polypeptide vaccine, enzyme, endorphin, glycoprotein, lipoprotein, or polypeptide involved in the blood coagulation cascade, that exerts its pharmacological effect systemically.

5. The composition of claim 1, wherein said polypeptide has a molecular weight of less than 30 kD.

6. The composition of claim 1, wherein said polypeptide has a molecular weight of less than 25 kD.

7. The composition of claim 1, wherein said polypeptide has a molecular weight of less than 20 kD.

8. The composition of claim 1, wherein said polypeptide has a molecular weight of less than 15 kD.

9. The composition of claim 1, wherein said polypeptide has a molecular weight of less than 10 kD.

10. The composition of claim 1, wherein at least one of said one or more surfactant compounds is a bile salt, an alkyl glycoside, a cyclodextrin or derivative thereof, a single-chain phospholipid, or a double-chain phospholipid in which each chain of the double-chain phospholipid is eight or fewer carbon atoms in length.

11. The composition of claim 1, wherein at least one of said one or more surfactant compounds is a salt of a fatty acid.

12. The composition of claim 11, wherein said fatty acid has 10–14 carbon atoms.

13. The composition of claim 12, wherein said fatty acid is capric acid.

14. The composition of claim 1, wherein at least one of said one or more surfactant compounds is sodium caprate.

15. A method for systemic administration of a biologically active polypeptide to a patient, comprising
providing the composition of claim 1; and
causing said patient to inhale said composition from a dry powder inhaler device for a time and under conditions effective for the polypeptide to be absorbed through epithelial cells of the lower respiratory tract.

16. The method of claim 15, wherein said dry powder is provided in said dry powder inhaler device in the form of agglomerates of said particles, said agglomerates being substantially deagglomerated prior to entering the respiratory tract of said patient.

17. The method of claim 15 wherein the polypeptide is a polypeptide hormone.

18. The method of claim 17, wherein said hormone is vasopressin, desmopressin, glucagon, corticotropin (ACTH), gonadotropin (luteinizing hormone, or LHRH), calcitonin, C-peptide of insulin, parathyroid hormone (PTH), human growth hormone (hGH), growth hormone (HG), growth hormone releasing hormone (GHRH), oxytocin, corticotropin releasing hormone (CRH), somatostatin, gonadotropin agonist, human atrial natriuretic peptide (hANP), recombinant human thyroxine releasing hormone (TRHrh), follicle stimulating hormone (FSH), or prolactin.

19. The method of claim 15 wherein the surfactant compound is a salt of a fatty acid.

20. The method of claim 19 wherein the surfactant compound is sodium caprate.

21. The composition of claim 1, wherein at least one of said one or more surfactant compounds is a bile salt.

22. The composition of claim 21, wherein said bile salt is sodium taurocholate.

23. The method of claim 15, wherein said polypeptide is a growth factor, interleukin, polypeptide vaccine, enzyme, endorphin, glycoprotein, lipoprotein, or polypeptide involved in the blood coagulation cascade.

24. The method of claim 15, wherein said polypeptide has a molecular weight of less than 30 kD.

25. The method of claim 15, wherein said polypeptide has a molecular weight of less than 25 kD.

26. The method of claim 15, wherein said polypeptide has a molecular weight of less than 20 kD.

27. The method of claim 15, wherein said polypeptide has a molecular weight of less than 15 kD.

28. The method of claim 15, wherein said polypeptide has a molecular weight of less than 10 kD.

29. The method of claim 15, wherein said surfactant compound is an alkyl glycoside, a cyclodextrin or derivative thereof, a single chain phospholipid, or a double-chain phospholipid in which each chain of the double-chain phospholipid is eight or fewer carbon atoms in length.

30. The method of claim 19, wherein said fatty acid has 10–14 carbon atoms.

31. The method of claim 19, wherein said fatty acid is capric acid.

32. The method of claim 15, wherein said surfactant compound is a bile salt.

33. The method of claim 32, wherein said bile salt is sodium taurocholate.

34. A dry powder inhaler device containing the composition of claim 1.

35. The dry powder inhaler device of claim 34, wherein said polypeptide is a polypeptide hormone.

36. The dry powder inhaler device of claim 35, wherein said hormone is vasopressin, desmopressin, glucagon, corticotropin (ACTH), gonadotropin (luteinizing hormone, or LHRH), calcitonin, C-peptide of insulin, parathyroid hormone (PTH), human growth hormone (hGH), growth hormone (HG), growth hormone releasing hormone (GHRH), oxytocin, corticotropin releasing hormone (CRH), somatostatin, gonadotropin agonist, human atrial natriuretic peptide (hANP), recombinant human thyroxine releasing hormone (TRHrh), follicle stimulating hormone (FSH), or prolactin.

37. The dry powder inhaler device of claim 34, wherein said polypeptide is a growth factor, interleukin, polypeptide vaccine, enzyme, endorphin, glycoprotein, lipoprotein, or polypeptide involved in the blood coagulation cascade.

38. The dry powder inhaler device of claim 34, wherein said polypeptide has a molecular weight of less than 30 kD.

39. The dry powder inhaler device of claim 34, wherein said polypeptide has a molecular weight of less than 25 kD.

40. The dry powder inhaler device of claim 34, wherein said polypeptide has a molecular weight of less than 20 kD.

41. The dry powder inhaler device of claim 34, wherein said polypeptide has a molecular weight of less than 15 kD.

42. The dry powder inhaler device of claim 34, wherein said polypeptide has a molecular weight of less than 10 kD.

43. The dry powder inhaler device of claim 34, wherein said surfactant compound is an alkyl glycoside, a cyclodextrin or derivative thereof, or a phospholipid.

44. The dry powder inhaler device of claim 34, wherein said surfactant is a salt of a fatty acid.

45. The dry powder inhaler device of claim 44, wherein said fatty acid has 10–14 carbon atoms.

46. The dry powder inhaler device of claim 45, wherein said fatty acid is capric acid.

47. The dry powder inhaler device of claim 34, wherein said surfactant is sodium caprate.

48. The dry powder inhaler device of claim 34, wherein said surfactant compound is a bile salt.

49. The dry powder inhaler device of claim 48, wherein said bile salt is sodium taurocholate.

50. The dry powder inhaler device of claim 34, wherein said primary particles are formed into agglomerates, said device being configured to induce the majority of said agglomerates to break down into particles having a diameter less than 10 microns or equal to about 10 microns, upon inhalation of said agglomerates from said device.

51. The dry powder inhaler device of claim 34, said inhaler device being a multi dose, breath actuated, dry powder inhaler for multiple use.

52. The composition of claim 1, wherein the primary particles are agglomerated.

53. A propellant-free composition consisting of
   (A) a polypeptide;
   (B) a surfactant compound that (i) has a consistency that permits it to be processed into primary particles having a diameter less than 10 microns, and (ii) enhances the systemic absorption of said polypeptide in the lower respiratory tract of a patient; and,
   (C) one or more additives selected from the group consisting of a mono- or disaccharide, raffinose, melezitose, sugar alcohol and polyol, said composition being in the form of a dry powder suitable for inhalation from a dry powder inhaler device and into the lower respiratory tract, wherein at least 50% of the total mass of (A) and (B) consists of primary particles having a diameter less than 10 microns or equal to about 10 microns, and wherein the surfactant compound is selected from the group consisting of a salt of a fatty acid, bile salt, single-chain phospholipid, double-chain phospholipid in which each chain of the double-chain phospholipid is eight or fewer carbon atoms in length, alkyl glycoside, cyclodextrin or derivative thereof, salt of a glycyrrhizine acid, salt of a saponin glycoside, salt of an acyl carnitine, and sodium salicylate.

54. The composition of claim 53, wherein the one or more additives comprise either
   (a) particles having a diameter of less than 10 microns or equal to about 10 microns, such that at least 50% of the composition consists of primary particles having a diameter of less than 10 microns or equal to about 10 microns; or
   (b) coarse particles having a diameter of at least 20 microns, such that an ordered mixture is formed between (i) the one or more additives, and (ii) the polypeptide of (A) and the surfactant compound of (B).

55. The composition of claim 53, wherein the polypeptide is a polypeptide hormone.

56. The composition of claim 55, wherein said hormone is vasopressin, desmopressin, glucagon, corticotropin (ACTH), gonadotropin (luteinizing hormone, or LHRH), calcitonin, C-peptide of insulin, parathyroid hormone (PTH), human growth hormone (hGH), growth hormone (HG), growth hormone releasing hormone (GHRH), oxytocin, corticotropin releasing hormone (CRH), somatostatin, gonadotropin agonist, human atrial natriuretic peptide (hANP), recombinant human thyroxine releasing hormone (TRHrh), follicle stimulating hormone (FSH), or prolactin.

57. The composition of claim 53, wherein the polypeptide is a growth factor, interleukin, polypeptide vaccine, enzyme, endorphin, glycoprotein, lipoprotein, or polypeptide involved in the blood coagulation cascade, that exerts its pharmacological effect systemically.

58. The composition of claim 53, wherein the polypeptide has a molecular weight of less than 30 kD.

59. The composition of claim 53, wherein the polypeptide has a molecular weight of less than 25 kD.

60. The composition of claim 53, wherein the polypeptide has a molecular weight of less than 20 kD.

61. The composition of claim 53, wherein the polypeptide has a molecular weight of less than 15 kD.

62. The composition of claim 53, wherein the polypeptide has a molecular weight of less than 10 kD.

63. The composition of claim 53, wherein the surfactant compound is a bile salt, an alkyl glycoside, a cyclodextrin or derivative thereof, a single-chain phospholipid, or a double-chain phospholipid in which each chain of the double-chain phospholipid is eight or fewer carbon atoms in length.

64. The composition of claim 53, wherein the surfactant compound is a salt of a fatty acid.

65. The composition of claim 64, wherein the fatty acid has 10–14 carbon atoms.

66. The composition of claim 65, wherein the fatty acid is capric acid.

67. The composition of claim 53, wherein the surfactant compound is sodium caprate.

68. The composition of claim 53, wherein the surfactant compound is a bile salt.

69. The composition of claim 53, wherein the primary particles are agglomerated.

70. The composition of claim 53, wherein the one or more additives are selected from the group consisting of lactose, glucose, raffinose, melezitose, lactitol, maltitol, trehalose, sucrose, and mannitol.

* * * * *